US00PP22103P2

(12) United States Plant Patent
Egger

(10) Patent No.: US PP22,103 P2
(45) Date of Patent: Aug. 30, 2011

(54) ***HEUCHERA* PLANT NAMED 'AUTUMN LEAVES'**

(50) Latin Name: ***Heuchera* spp.**
Varietal Denomination: Autumn Leaves

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,256

(22) Filed: May 11, 2010

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu

(74) *Attorney, Agent, or Firm* — Klarquist Sparkman, LLP

(57) ABSTRACT

A new and distinct hybrid of *Heuchera* plant characterized by leaves colored brick red in spring and fall and amber and tan in summer, bicolor red purple and light pink flowers, and excellent tolerance to heat and humidity.

1 Drawing Sheet

Botanical denomination: *Heuchera* spp.
Variety designation: 'Autumn Leaves'.

BACKGROUND OF THE INVENTION

The present invention relates to a new and distinct cultivar of *Heuchera* hybrid and given the cultivar name of 'Autumn Leaves'. *Heuchera* is in the family *Saxifragaceae. Heuchera* 'Autumn Leaves' originated from a planned breeding cross between *Heuchera* 763-1, a proprietary unreleased plant, as the seed parent, and *Heuchera* 834-8, a proprietary unreleased plant, as the pollen parent. Compared to the seed parent the new cultivar has foliage colored rose red rather than rose purple and a light rather than a heavy veil. Compared to the pollen parent the new cultivar has a lighter veil and red rather than rose to khaki colored leaves. Compared to *Heuchera* 'Fire Chief' (U.S. patent application No. 12/653,630), the new cultivar is a different shade of red and is lightly veiled rather than not veiled. The leaves of the new cultivar are larger and the inflorescences are taller than *Heuchera* 'Fire Chief' and the leaves are not shiny like *Heuchera* 'Fire Chief'.

This new *Heuchera* is distinguished by:

1. leaves colored brick red in spring and fall and amber and tan in summer,
2. bicolor red purple and light pink flowers,
3. excellent tolerance to heat and humidity.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
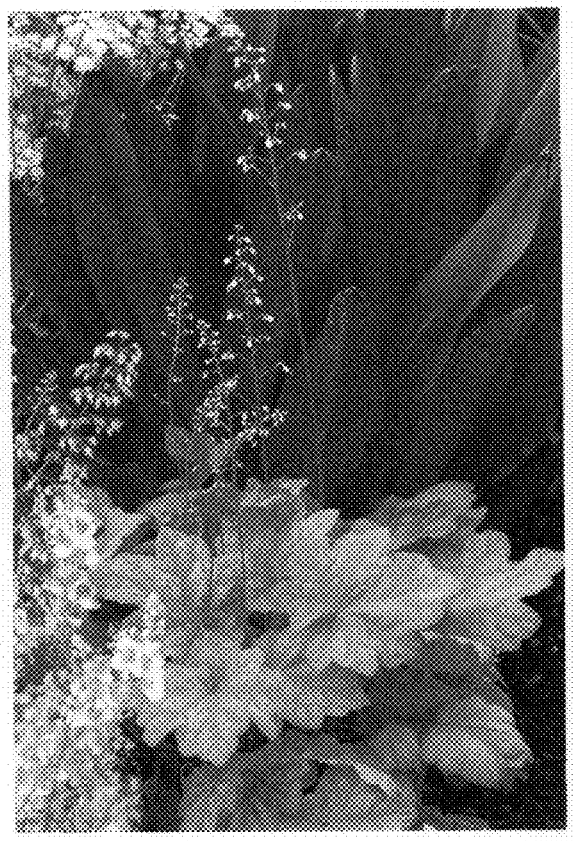
FIG. 1 shows a one-year-old plant of *Heuchera* 'Autumn Leaves' growing in the ground in part sun in the garden in June in Canby, Oreg.
Figure 2:
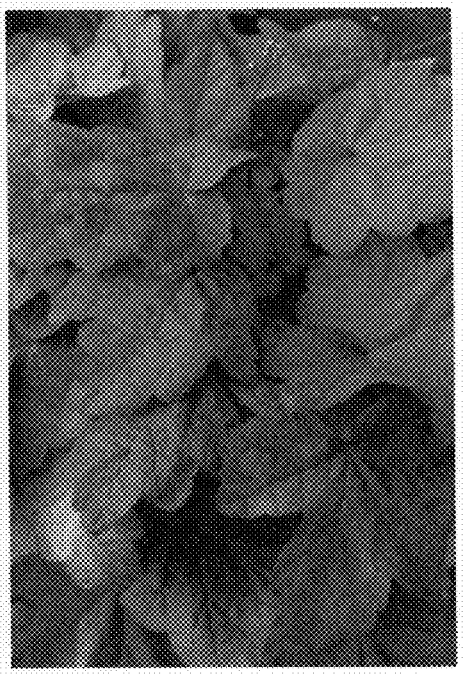
FIG. 2 shows a plant with fall color in October in Canby, Oreg.

The following is a detailed description of the new *Heuchera* cultivar based on observations taken in June of a one-year-old specimen grown in a one gallon container in a shade house in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 5th edition.

Plant:

*Form.*—Basal rosette, herbaceous perennial.
*Hardiness.*—USDA Zone 4 to 9.
*Size.*—16 cm tall from top of the foliage to the ground and 55 cm wide.
*Habit.*—Mounding.
*Crown number.*—5.
*Vigor.*—Good.
*Roots.*—Fibrous, freely branching, fine, and white in color; roots develop easily from cuttings.

Leaf:

*Type.*—Simple.
*Arrangement.*—Rosette.
*Shape.*—Broadly ovate.
*Lobing/division.*—5 to 9 shallow lobes.
*Venation.*—Palmate.
*Margins.*—Crenate.
*Apex.*—Mucronulate.
*Base.*—Cordate, lobes overlapping at the base.
*Blade size.*—Grows to 14.5 cm long and 12 cm wide.
*Surface texture.*—Glandular on both sides.
*Petiole description.*—Grows to 16 cm long and 2 mm wide, glandular hairs, Greyed Purple 187C.
*Leaf color.*—Variable depending amount of light, temperature, and age of the leaf; spring and fall new growth topside Greyed Purple 184A with a pink veil, Greyed Purple 186A, bottom side Greyed Purple 187B; mature spring and fall leaves between Greyed Purple 183B and Brown 200B along margins and veins, veil Red Purple 59D, bottom side Greyed Purple 187B; summer topside Greyed Red 182C to 182B with veins Yellow Green 152C, bottom side 183D; winter topside is dull red, Greyed Purple 187A with areas of Greyed Purple 183A.

Inflorescence:

*Size.*—Grows to 18 cm long and 7 cm wide.

*Type.*—Thyrse.

*Number of flowers per thyrse.*—About 60 per thyrse.

*Number of thyrse.*—About 10 in first spring bloom.

*Peduncle.*—Grows to 41 cm tall, 3 mm wide at base, Greyed Purple 187B, glandular hairs, with no stem leaves.

*Pedicel.*—Variable in size, with glandular hairs, Greyed Purple 187A.

*Bloom period.*—June to July in Canby, Oreg.

Flower bud:

*Size.*—2.7 mm wide and 4 mm long.

*Description.*—Glandular puberulent, ovoid.

*Color.*—Red Purple 64B on top half and Red Purple 75C on bottom half.

Flower:

*Type.*—Perfect.

*Shape.*—Campanulate.

*Size.*—7 mm long and 4 mm wide.

*Petal description.*—5 in number, 3 mm long and 1 mm wide, reflexed, spatulate, tip obtuse, base attenuate, margin irregular, glabrous on top side, glandular on bottom side; White 155D with Red Purple 64C on tip on top and bottom.

*Calyx description.*—Campanulate, 6 mm long and 4 mm wide, with 5 lobes, divided ½ way to the base, glandular hairs on both sides; obtuse, entire, Red Purple 75C on top half and 71B on bottom half.

*Stamen description.*—5 in number, filaments 3 mm long, Red Purple 73D, anthers 0.5 mm, Yellow Orange 22B, pollen Yellow Orange 14D.

*Pistil description.*—1, 2-beaked, 4 mm long, Red Purple 75C overall, ovary 1 mm, style 3 mm long.

*Fragrance.*—None.

*Lastingness.*—Each thyrse blooms for about 2 weeks on the plant.

Fruit:

*Type.*—Two beaked capsule.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct hybrid of *Heuchera* plant as herein illustrated and described.

* * * * *